United States Patent
Kim et al.

(10) Patent No.: US 12,243,227 B2
(45) Date of Patent: Mar. 4, 2025

(54) REAL-TIME ACOUSTIC SIMULATION METHOD BASED ON ARTIFICIAL INTELLIGENCE, AND ULTRASOUND TREATMENT SYSTEM USING THE SAME

(71) Applicant: KOREA INSTITUTE OF SCIENCE AND TECHNOLOGY, Seoul (KR)

(72) Inventors: Hyung Min Kim, Seoul (KR); Kyungho Yoon, Seoul (KR); Tae Young Park, Seoul (KR); Heekyung Koh, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 401 days.

(21) Appl. No.: 17/710,026

(22) Filed: Mar. 31, 2022

(65) Prior Publication Data

US 2022/0319001 A1 Oct. 6, 2022

(30) Foreign Application Priority Data

Mar. 31, 2021 (KR) .................. 10-2021-0041991

(51) Int. Cl.
*G06T 7/00* (2017.01)
*G16H 20/30* (2018.01)
*A61N 7/00* (2006.01)

(52) U.S. Cl.
CPC .......... *G06T 7/0012* (2013.01); *G16H 20/30* (2018.01); *A61N 7/00* (2013.01);
(Continued)

(58) Field of Classification Search
None
See application file for complete search history.

(56) References Cited

U.S. PATENT DOCUMENTS

| | | |
|---|---|---|
| 2011/0235884 A1 | 9/2011 | Schreibmann et al. |
| 2021/0045715 A1 | 2/2021 | Mauldin et al. |
| 2022/0066905 A1 | 3/2022 | Lee et al. |

FOREIGN PATENT DOCUMENTS

| | | |
|---|---|---|
| JP | 2019-209130 A | 12/2019 |
| KR | 10-2020-0021398 A | 2/2020 |

(Continued)

OTHER PUBLICATIONS

H., Pahk, K.J., Park, S. and Kim, H., 2019. Development of a subject-specific guide system for Low-Intensity Focused Ultrasound (LIFU) brain stimulation. Computer methods and programs in biomedicine, 176, pp. 105-110.*

(Continued)

*Primary Examiner* — Zhitong Chen
(74) *Attorney, Agent, or Firm* — NSIP Law

(57) ABSTRACT

A real-time acoustic simulation method based on artificial intelligence according to an embodiment of the present disclosure includes acquiring medical image data of a target area to be treated; determining ultrasound parameters related to the output of an ultrasonic transducer based on the medical image data; inputting the ultrasound parameters to a numerical model to generate a numerical model based acoustic simulation image for a specific position of the ultrasonic transducer; training an artificial intelligence model using the medical image data and the numerical model based acoustic simulation image; generating an artificial intelligence model based acoustic simulation image for an arbitrary position of the ultrasonic transducer using the trained artificial intelligence model; and outputting a real-time acoustic simulation image with a position change of the ultrasonic transducer.

13 Claims, 13 Drawing Sheets
(12 of 13 Drawing Sheet(s) Filed in Color)

(52) U.S. Cl.
CPC .............. *G06T 2207/10081* (2013.01); *G06T 2207/10088* (2013.01); *G06T 2207/10132* (2013.01); *G06T 2207/20081* (2013.01)

(56) References Cited

FOREIGN PATENT DOCUMENTS

| KR | 10-2020-0092447 A | 8/2020 |
|----|-------------------|--------|
| KR | 10-2021-0002197 A | 1/2021 |
| KR | 10-2235681 B1 | 4/2021 |

OTHER PUBLICATIONS

Park, T.Y., Pahk, K.J. and Kim, H., 2019. Method to optimize the placement of a single-element transducer for transcranial focused ultrasound. Computer Methods and Programs in Biomedicine, 179, p. 104982.*

Pasquinelli, C., Montanaro, H., Lee, H.J., Hanson, L.G., Kim, H., Kuster, N., Siebner, H.R., Neufeld, E. and Thielscher, A., 2020. Transducer modeling for accurate acoustic simulations of transcranial focused ultrasound stimulation. Journal of neural engineering, 17(4), p. 046010.*

Tamaddon-Jahromi, H.R., Chakshu, N.K., Sazonov, I., Evans, L.M., Thomas, H. and Nithiarasu, P., 2020. Data-driven inverse modelling through neural network (deep learning) and computational heat transfer. Computer Methods in Applied Mechanics and Engineering, 369, p. 113217.*

Sanchez-Gonzalez, Alvaro, et al. "Learning to Simulate Complex Physics with Graph Networks." *International Conference on Machine Learning PMLR*, arXiv:2002.09405v2 Sep. 14, 2020 (20 pages in English).

Stanziola, Antonio, et al. "A Helmholtz equation solver using unsupervised learning: Application to transcranial ultrasound." *Journal of Computational Physics* vol. 441, 2021: 110430 (19 pages in English).

* cited by examiner

REAL-TIME ACOUSTIC SIMULATION METHOD BASED ON ARTIFICIAL INTELLIGENCE, AND ULTRASOUND TREATMENT SYSTEM USING THE SAME

DESCRIPTION OF GOVERNMENT-FUNDED RESEARCH AND DEVELOPMENT

This research is conducted by Korea Evaluation Institute of Industrial Technology under the support of Ministry of Trade, Industry and Energy (Project name: Development of technology for personalized B2B (Brain to Brain) cognitive enhancement based on high resolution noninvasive bidirectional neural interfaces, Project No.: 1415169864).

This research is conducted by National Research Council of Science & Technology under the support of Ministry of Science and ICT (Project name: Development of technology for overcoming barriers to stroke patients based on personalized neural plasticity assessment and enhancement, Project No.: CAP-18-01-KIST).

CROSS-REFERENCE TO RELATED APPLICATION

This application claims priority to Korean Patent Application No. 10-2021-0041991, filed on Mar. 31, 2021, and all the benefits accruing therefrom under 35 U.S.C. § 119, the contents of which in its entirety are herein incorporated by reference.

BACKGROUND

Field

The present disclosure relates to a method for outputting acoustic simulation results in real-time with a position change of an ultrasonic transducer using an artificial intelligence model capable of machine learning and an ultrasound treatment system using the method.

Description of Related Art

Conventionally, the insertion of electrodes into a patient's body has been used to conduct therapy for the patient's pain relief or stimulation of the nerve cell of the specific body part, but there is the risk of damage to the human body by the physically invasive process.

Recently, ultrasound stimulation therapy that stimulates an affected part without a physically invasive process is widely used, and ultrasound may be classified into High-intensity Focused Ultrasound (HIFU) and Low-intensity Focused Ultrasound (LIFU) according to the output intensity. The HIFU is used in direct treatment for thermally and mechanically removing living tissues such as cancer cells, tumors, and lesions, while the LIFU is widely used to treat brain diseases such as Alzheimer's disease and depression by stimulating brain nerves or can be used in rehabilitation therapy to induce neuromuscular activation by stimulation. The focused ultrasound treatment technology is gaining attention due to its minimally invasive process with fewer side effects such as infection or complications.

The focused ultrasound is used to stimulate or remove a target area as it goes through body tissues such as skin and bones, and the travel path may be changed by various factors such as the thickness or shape of each area and the frequency of the output ultrasound. In a surgery requiring high precision, such as brain surgery, there is a high likelihood that even a small difference in the path leads to a severe side effect, so it is necessary to perform a task of accurately simulating the travel path and focal position of ultrasound based on the various factors such as the structure of a patient's skull and the ultrasound parameters.

Most of the existing acoustic simulation acquires the results of the sonication path and the focal position based on a given environmental factor and input ultrasound parameters using a numerical model that outputs direct calculation results. For example, when computed tomography (CT) or magnetic resonance imaging (MRI) images of a patient's body part and ultrasound parameters (factor related to the output of a transducer) are entered, a computer processor estimates ultrasound simulation results through a series of programs and outputs in the form of an image.

The acoustic simulation based on a numerical model can acquire relatively accurate simulation results with the help of the computer performance improvement, but it requires 30 seconds to 10 minutes to obtain the simulation results for a single preset transducer position, and cannot provide results for a position on which simulation has not been performed, so the acoustic simulation based on a numerical model needs to be performed for every possible position.

RELATED LITERATURES (Patent Literature 1) US Patent Publication No. 2011-0235884

SUMMARY

The present disclosure is directed to providing a method for acquiring real-time acoustic simulation results for an arbitrary position of an ultrasonic transducer using a trained artificial intelligence model.

The present disclosure is further directed to providing a focused ultrasound treatment system capable of precise ultrasound treatment using real-time acoustic simulation images based on artificial intelligence.

A real-time acoustic simulation method based on artificial intelligence according to an embodiment of the present disclosure is performed by a processor, and includes acquiring medical image data of a target area to be treated; determining ultrasound parameters related to the output of an ultrasonic transducer based on the medical image data; inputting the ultrasound parameters to a numerical model to generate a numerical model based acoustic simulation image for a specific position of the ultrasonic transducer; training an artificial intelligence model using the medical image data and the numerical model based acoustic simulation image; generating an artificial intelligence model based acoustic simulation image for an arbitrary position of the ultrasonic transducer using the trained artificial intelligence model; and outputting a real-time acoustic simulation image with a position change of the ultrasonic transducer.

According to an embodiment, training the artificial intelligence model may include inputting the medical image data and the numerical model based acoustic simulation image as training data; generating an acoustic simulation image corresponding to a specific position of the ultrasonic transducer using a generator; acquiring error data by comparing the acoustic simulation image generated by the generator with the numerical model based acoustic simulation image using a discriminator; and training the generator using the error data.

According to an embodiment, the artificial intelligence model may be trained to reduce differences between the generator's acoustic simulation image and the numerical model-based acoustic simulation image by iteratively performing the training step.

According to an embodiment, the generator may include at least one convolutional layer for receiving the input medical image data and outputting a feature map that emphasizes features of a region of interest; and at least one transposed convolutional layer for generating the acoustic simulation image corresponding to the medical image data based on the feature map.

According to an embodiment, the discriminator may include at least one convolutional layer for receiving the input acoustic simulation image generated by the generator and outputting a feature map that emphasizes features of a region of interest.

According to an embodiment, the artificial intelligence model may generate the acoustic simulation image corresponding to the medical image data through trained nonlinear mapping.

According to an embodiment, the medical image data may include a computed tomography (CT) image or a magnetic resonance imaging (MRI) image.

There may be provided a computer program stored in a computer-readable recording medium for performing the real-time acoustic simulation method based on artificial intelligence according to an embodiment.

An ultrasound treatment system based on artificial intelligence according to an embodiment of the present disclosure includes an input unit to receive input medical image data of a target area to be treated; an ultrasound output unit to output ultrasound to the target area; a location tracking unit to acquire position information of the ultrasound output unit in real-time; a processing unit to generate a real-time acoustic simulation image with a position change of the ultrasound output unit using the real-time acoustic simulation method based on artificial intelligence; and a display unit to display the real-time acoustic simulation image.

According to an embodiment, the ultrasound output unit may be configured to output high-intensity focused ultrasound to thermally or mechanically remove a target tissue or low-intensity focused ultrasound to stimulate the target tissue without damage.

A real-time acoustic simulation method based on artificial intelligence according to another embodiment of the present disclosure is performed by a processor, and includes acquiring medical image data of a target area to be treated and reference position information of an ultrasonic transducer; generating an acoustic simulation image for an arbitrary position of the ultrasonic transducer using an artificial intelligence model trained to generate the acoustic simulation image in response to a position change of the ultrasonic transducer; and outputting the acoustic simulation image.

According to an embodiment, the artificial intelligence model may be trained to reduce differences between the acoustic simulation image generated by the generator and a numerical model based acoustic simulation image by iteratively performing the steps of receiving input of the medical image data and the numerical model based acoustic simulation image as training data; generating an acoustic simulation image corresponding to a specific position of the ultrasonic transducer using a generator; acquiring error data by comparing the acoustic simulation image generated by the generator with the numerical model based acoustic simulation image using a discriminator; and training the generator using the error data.

According to an embodiment of the present disclosure, it is possible to acquire acoustic simulation results for an arbitrary transducer position at which simulation has never been performed before using an artificial intelligence model trained with medical image data (computed tomography (CT) images, magnetic resonance imaging (MRI) images) and numerical model-based simulation results. The existing method that estimates ultrasound output results through direct calculation needs to perform simulation for as many transducer positions as possible, and requires a few minutes or more for each position, which makes real-time simulation impossible. By contrast, according to the method of the present disclosure, it is possible to perform real-time acoustic simulation at a very high speed for positions not included in the existing training data (i.e., positions at which calculation-based simulation has not been performed) using the artificial intelligence model. Using this, medical staff can see simulation images in real-time with the movement of an ultrasonic transducer, thereby achieving more precise and faster treatment.

BRIEF DESCRIPTION OF DRAWINGS

The patent or application file contains at least one drawing executed in color. Copies of this patent or patent application publication with color drawing(s) will be provided by the Office upon request and payment of the necessary fee.

The following is a brief introduction to necessary drawings in the description of the embodiments to describe the technical solutions of the embodiments of the present disclosure or the existing technology more clearly. It should be understood that the accompanying drawings are for the purpose of describing the embodiments of the present disclosure and are not intended to be limiting of the present disclosure. Additionally, for clarity of description, illustration of some elements in the accompanying drawings may be exaggerated and omitted.

DETAILED DESCRIPTION

Figure 1:
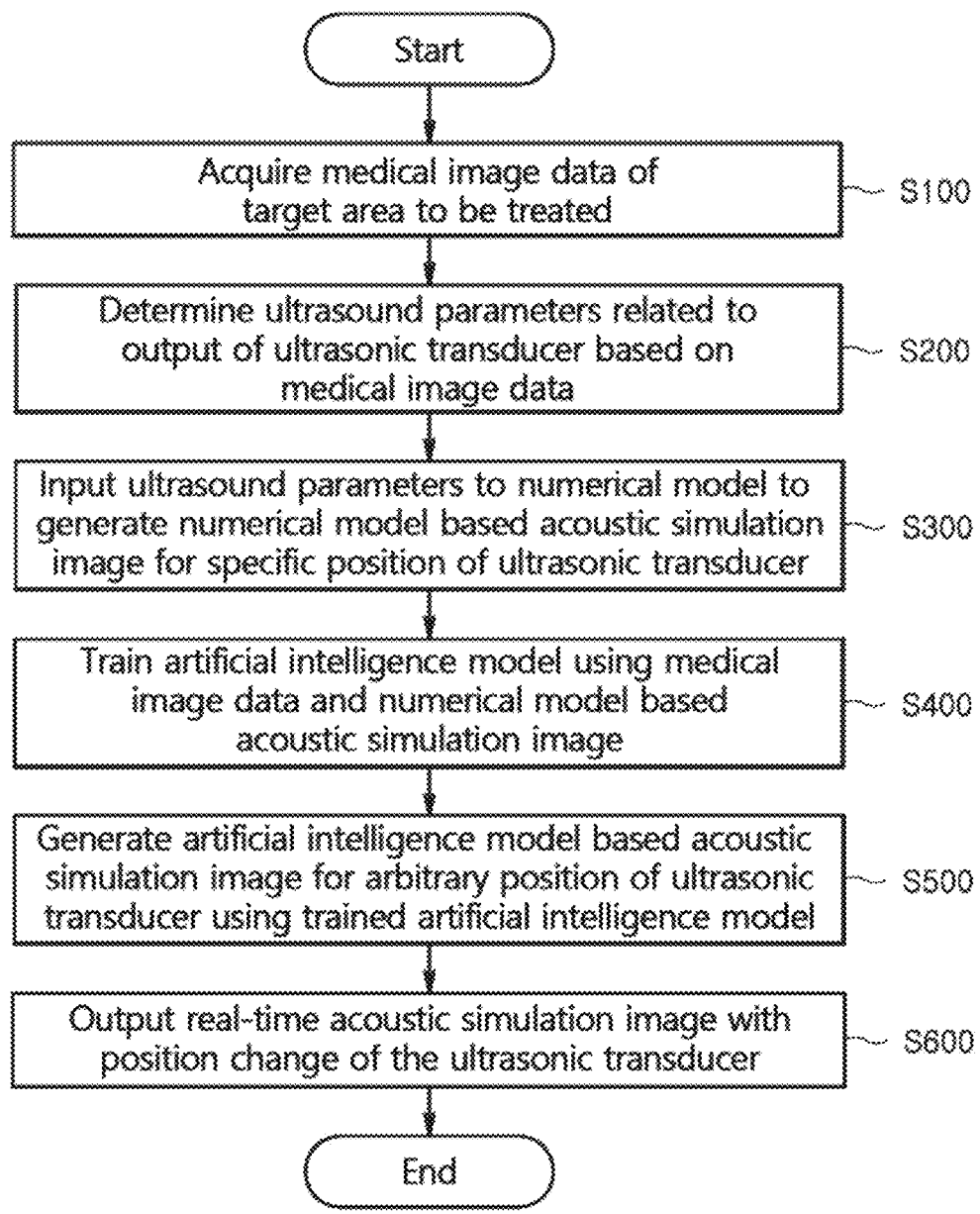
FIG. 1 is a flowchart illustrating a real-time acoustic simulation method based on artificial intelligence according to an embodiment.

The following detailed description of the present disclosure is made with reference to the accompanying drawings, in which particular embodiments for practicing the present disclosure are shown for illustrative purposes. These embodiments are described in sufficiently detail for those skilled in the art to practice the present disclosure. It should be understood that various embodiments of the present disclosure are different but do not need to be mutually exclusive. For example, particular shapes, structures, and features described herein in connection with one embodiment may be embodied in another embodiment without departing from the spirit and scope of the present disclosure. It should be further understood that changes may be made to the positions or placement of individual elements in each disclosed embodiment without departing from the spirit and scope of the present disclosure. Accordingly, the following detailed description is not intended to be taken in limiting senses, and the scope of the present disclosure, if appropriately described, is only defined by the appended claims along with the full scope of equivalents to which such claims are entitled. In the drawings, similar reference signs denote the same or similar functions in many aspects.

The terms as used herein are general terms selected as those being now used as widely as possible in consideration of functions, but they may differ depending on the intention of those skilled in the art or the convention or the emergence of new technology. Additionally, in certain cases, there may be terms arbitrarily selected by the applicant, and in this case, the meaning will be described in the corresponding description part of the specification. Accordingly, it should be noted that the terms as used herein should be interpreted based on the substantial meaning of the terms and the context throughout the specification, rather than simply the name of the terms.

Hereinafter, exemplary embodiments of the present disclosure will be described in detail with reference to the accompanying drawings.

Real-Time Acoustic Simulation Method Based on Artificial Intelligence

FIG. 1 is a flowchart illustrating the real-time acoustic simulation method based on artificial intelligence according to an embodiment.

Figure 2:
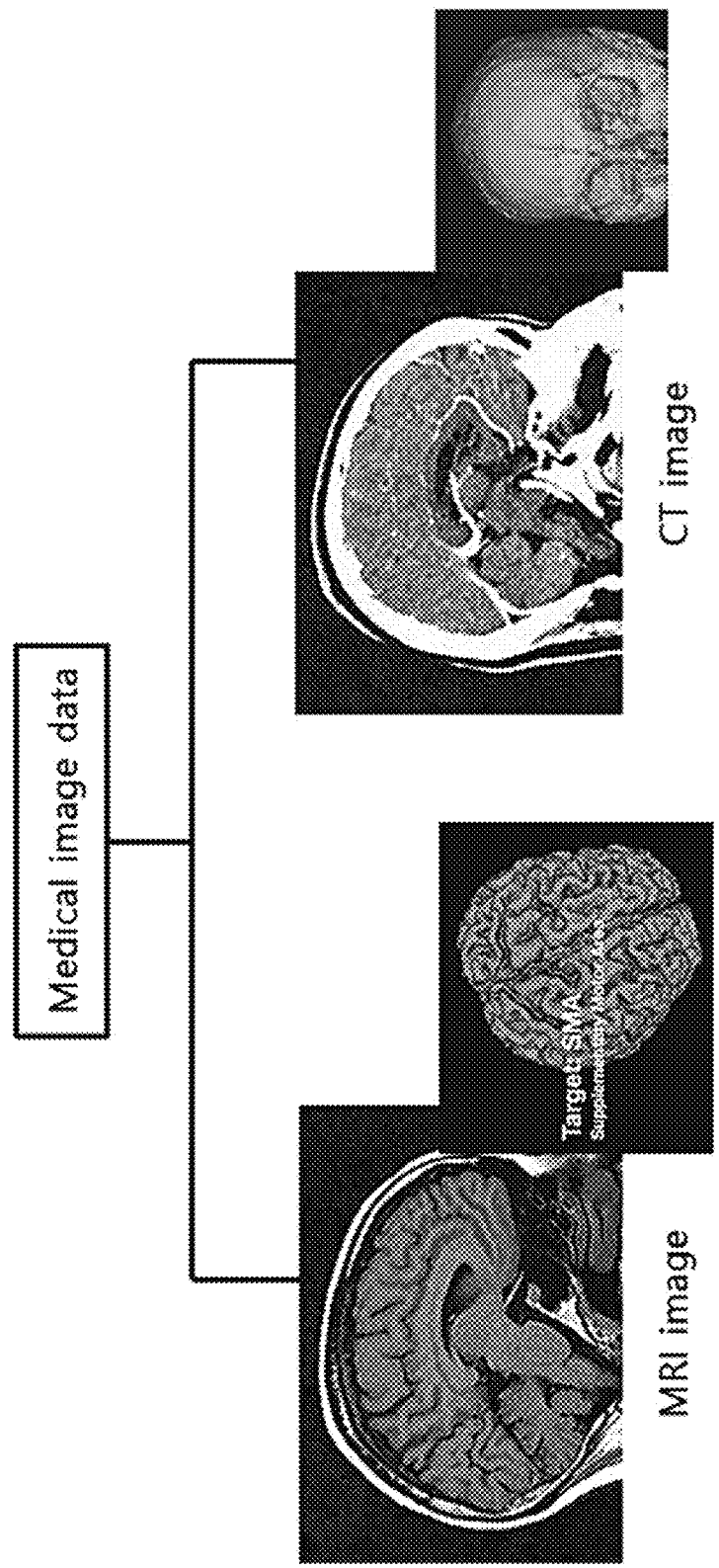
FIG. 2 shows the type of medical image data used in the acoustic simulation.

Referring to FIG. 1, to begin with, the step of acquiring medical image data of a patient's target area to be treated is performed (S100). The medical image data is used to determine ultrasound parameters or generate an acoustic simulation image, and may be used to train an artificial intelligence model. FIG. 2 shows the type of exemplary medical image data. As shown, the medical image data includes a computed tomography (CT) image or a magnetic resonance imaging (MRI) image. According to an embodiment, the method may further include preprocessing the acquired image data, and the preprocessing process includes a process of dividing each image into a region of interest and background and removing the background that is not necessary for training.

Subsequently, the step of determining ultrasound parameters related to the output of an ultrasonic transducer based on the medical image data (S200) is performed. In this step, a variety of variables of ultrasound that will be outputted from the transducer, such as frequency, waveform, and intensity, are determined based on the information, such as the shape and thickness of the skull, which can be identified from the CT or MRI image.

Subsequently, the step of inputting the determined ultrasound parameters to a numerical model and generating a numerical model-based acoustic simulation image for a specific position of the ultrasonic transducer (S300) is performed. The numerical model is configured to perform a preset calculation on an input value and output a corresponding result value, and in the specification, the numerical model refers to a system that outputs simulation results of the sonication path and focal position based on the input medical image and the determined ultrasound parameter (factor related to the output of the transducer) information.

Figure 3:
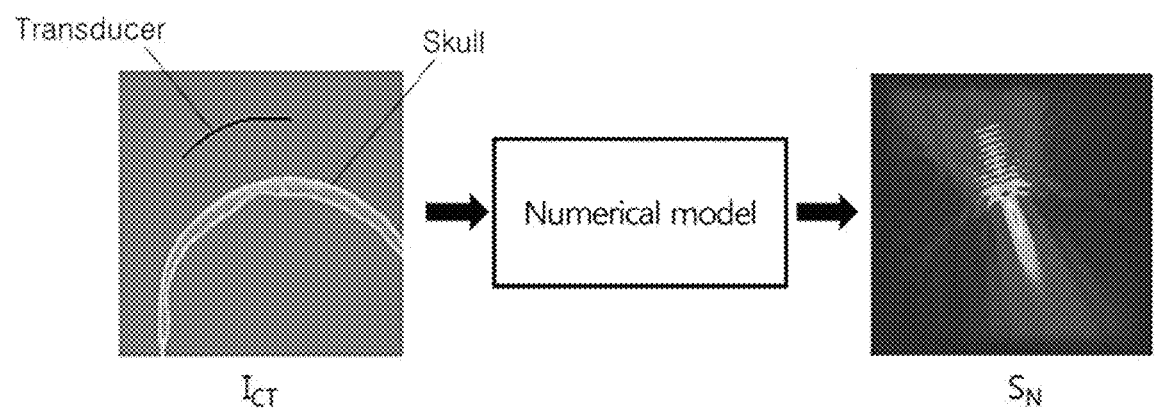
FIG. 3 shows a process of acquiring acoustic simulation results from an input computed tomography (CT) image using a numerical model.

FIG. 3 shows a process of acquiring the acoustic simulation results from the input CT image using the numerical model. As shown, when the CT image $I_{CT}$ showing the ultrasonic transducer disposed at the specific position and the skull shape is inputted to the numerical model, estimation results of the travel path, acoustic pressure level, and focal position of the output ultrasound of a specific parameter from the transducer of the corresponding position are outputted in the form of an image. The image acquired by the above-described process is referred to as a 'numerical model-based acoustic simulation image $S_N$'. As described above, the numerical model-based simulation requires a relatively long time of about 30 seconds to 10 minutes per transducer position.

Subsequently, the step of training the artificial intelligence model using the medical image data and the numerical model-based acoustic simulation image (S400) is performed. Machine learning is used for a computer to cluster or classify things or data, and typically includes support vector machines (SVM) and Neural Networks. The present disclosure employs a Generative Adversarial Network (GAN) model that improves the performance by adversarial training of a generator and a discriminator.

The artificial intelligence model according to an embodiment may be trained to extract features from an input image, generate an acoustic simulation image corresponding to the input image through trained nonlinear mapping, and output more precise results by comparing the generated simulation image with the real simulation image based on the numerical model.

Figure 4:
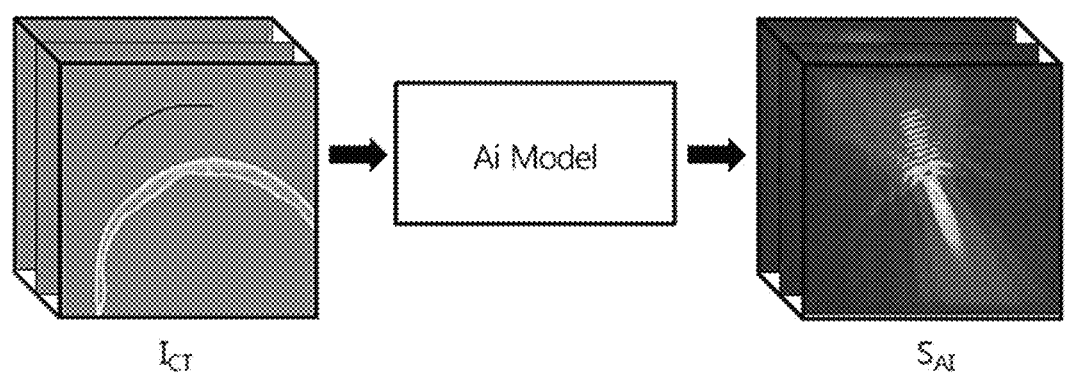
FIG. 4 shows a process of acquiring acoustic simulation results from an input CT image using an artificial intelligence model.

FIG. 4 shows a process of acquiring the acoustic simulation results from the input CT image using the artificial intelligence model. In the same way as the numerical model, when the CT image $I_{CT}$ showing the ultrasonic transducer disposed at the specific position and the skull shape is inputted to the artificial intelligence model, estimation results of the sonication path, acoustic pressure level, and focal position of the output ultrasound of a specific parameter from the transducer of the corresponding position are outputted in the form of an image. The image acquired by the above-described process is referred to as an 'artificial intelligence model based acoustic simulation image $S_{AI}$'. In the same way as the numerical model, the estimated acoustic simulation results are outputted, but the corresponding image is created through nonlinear mapping based on training, not direct calculation, so the required time is much shorter than the numerical model, which makes real-time simulation possible.

Figure 5:
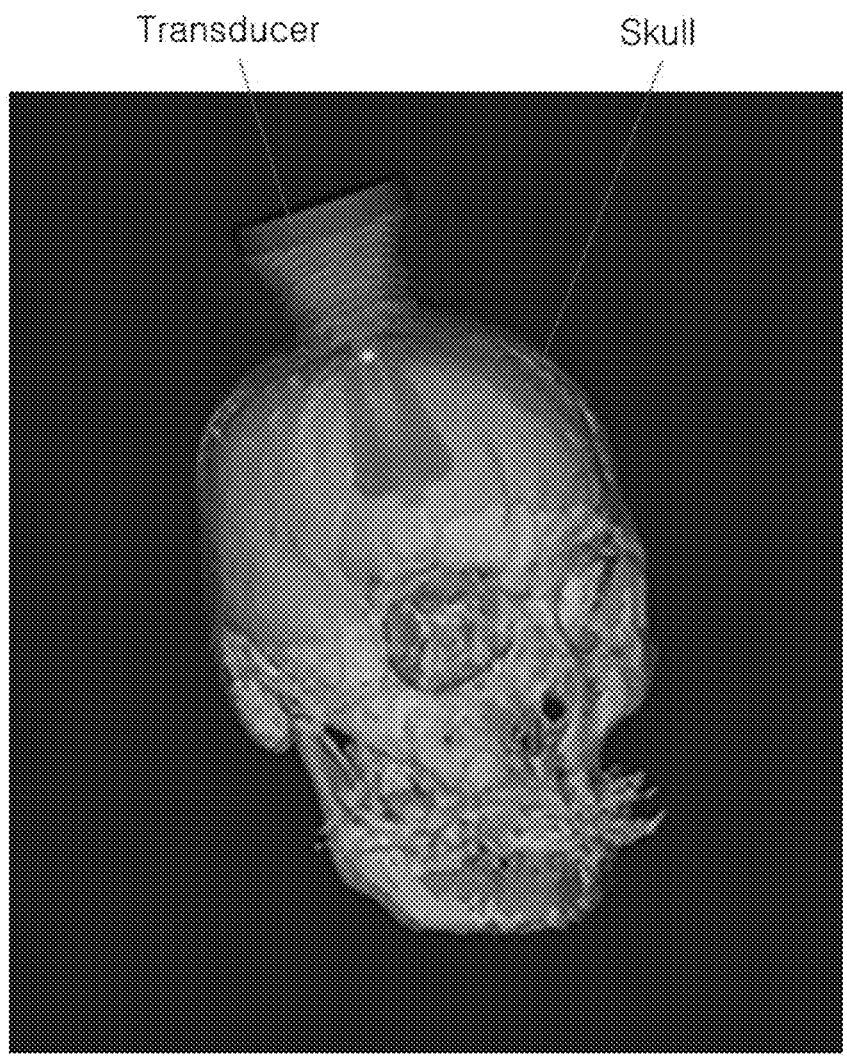
FIG. 5 shows a 3-dimensional (3D) image of acoustic simulation results according to an embodiment.

FIG. 5 shows a 3D image of the acoustic simulation results based on the artificial intelligence model according to an embodiment. As shown, information that changes as the output ultrasound of the transducer goes through the skull, such as the sonication path, focal position, and acoustic pressure level at each position, is displayed in color.

Figure 6:
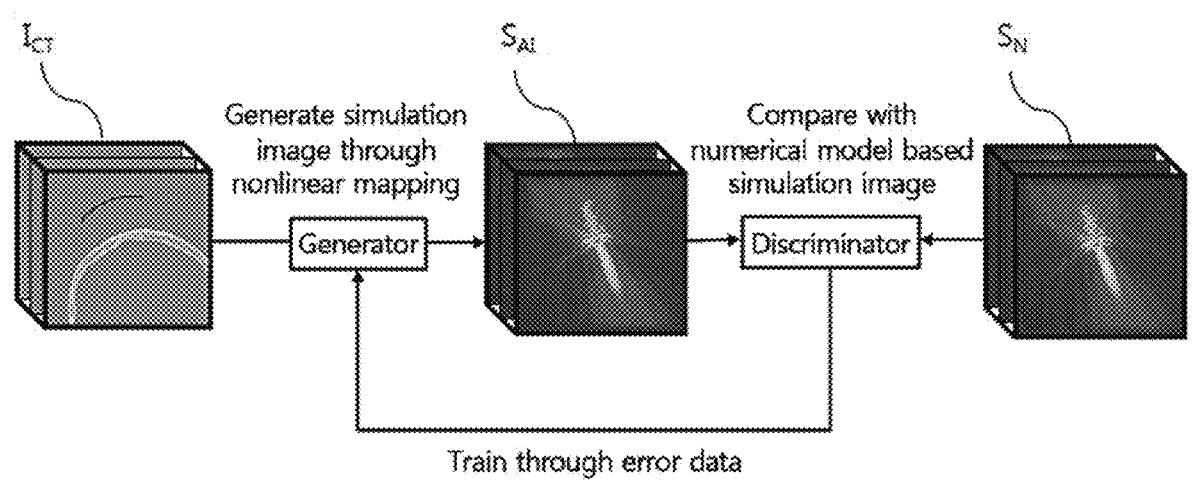
FIG. 6 shows a process of training an artificial intelligence model for acquiring acoustic simulation results according to an embodiment.

FIG. 6 shows a process of training the artificial intelligence model according to an embodiment. Referring to FIG. 6, the training process of the artificial intelligence model includes (i) inputting the medical image data $I_{CT}$ and the numerical model based acoustic simulation image $S_N$ as training data; (ii) generating the acoustic simulation image $S_{AI}$ corresponding to the specific position of the ultrasonic transducer using a generator; (iii) acquiring error data by comparing the acoustic simulation image $S_{AI}$ generated by the generator with the numerical model based acoustic simulation image $S_N$ using a discriminator; and (iv) training the generator using the error data. The artificial intelligence model has improved performance by iteratively performing the training step, thereby reducing differences between the acoustic simulation image $S_{AI}$ generated by the generator and the numerical model-based acoustic simulation image $S_N$.

According to an embodiment, the generator may include multiple layers, including at least one convolutional layer and at least one transposed convolutional layer. The convolutional layer receives input medical image data and outputs a feature map that emphasizes the features of a region of interest. Specifically, the convolutional layer outputs the feature map that emphasizes the features of an image area by multiplying the input data with filters while the filters move with a predetermined stride. As the image goes through the convolutional layer, the width, height, and depth of the image gradually decrease and the number of channels increases. The values of the filters include weight parameters, and the values of the filters are randomly set at the initial step, and in the training step, they are updated for optimization through error backpropagation (updating the weight parameters by propagating the output error of the output layer to the input layer).

The transposed convolutional layer is a layer that learns a process of synthesizing the feature maps extracted by the convolutional layer into a target output image and restoring the size (upsampling). The transposed convolutional layer outputs the feature maps by multiplying input data with filters while the filters move with a predetermined stride, and transposes the input/output size as opposed to the convolutional layer. That is to say, as the image goes through the transposed convolutional layer, the width, height, and depth of the image gradually increase, and the number of channels decreases. A new image (for example, an acoustic simulation image) is generated based on the extracted features by transposing the convolutional layer.

According to an embodiment, the convolutional layer or the transposed convolutional layer of the generator may be used together with batch normalization for normalizing the data distribution of the feature maps and an activation function for determining the range of each output value. The batch normalization serves to prevent overfitting in which the filter values (weights) of convolution or transposed convolution fit training data well and perform worse on test data in the training process, thereby stabilizing the training process. The feature maps are normalized through the mean and the standard deviation (as much as batch fed into the model) to stabilize the data distribution of the feature maps. After training, the actual input test data is also equally normalized through the mean and the standard deviation stored during the training process, thereby generating an output image from data having a different distribution from the training data more stably.

When combined with the convolutional layer or the transposed convolutional layer, the activation function determines the range of the output value that will be passed from each layer to another layer and sets a threshold value for deciding which values will be passed. Additionally, nonlinearity is added to a deep learning model, and by the addition of the nonlinearity, the layers of the deep learning model become deeper, and derivative values are very small and converge to 0, thereby reducing the Gradient vanishing effect that the weight parameters are not updated. The activation function may include, for example, ReLu activation function that when input data is equal to or smaller than 0, outputs 0, and when input data is larger than 0, preserves the value, LeakyReLu activation function, which plays a similar role to the ReLu activation function, but when the input value is smaller than 0, multiplies the input value by 0.1 to have a non-zero output, and when the input value is larger than 0, preserves the value, Tan h activation function that causes input data to have a value between −1 and 1, and Sigmoid activation function that causes input data to have a value between 0 and 1.

The discriminator may include at least one convolutional layer to receive the input acoustic simulation image generated by the generator and output a feature map that emphasizes features of a region of interest. As opposed to the generator, each convolutional layer of the discriminator is configured to receive the input acoustic simulation image and output the feature map that emphasizes features of a region of interest. In the same way as the generator, each convolutional layer may be used together with batch normalization for normalization of the data distribution of the feature map and an activation function for determining the range of each output value.

According to an embodiment, the generator may include at least one residual block layer, and since the deeper layers of the model make optimization more difficult, the residual block layer serves to facilitate the model training. The residual block layer is repeated between the convolutional layer (Encoder), which reduces the width and height of the image and widens channelwise, and the transposed convolutional layer (Decoder), which restores the width and height of the image and the channels into the original dimensions. One residual block includes convolution-batch normalization-ReLu activation-convolution-batch normalization, and here, the convolution outputs an image having the same width, height, depth, and channel size as the input image through adjustment of the filters and the stride values. That is, it is aimed at passing the input data to the next layer with minimized information loss, but not extracting or restoring the features of the input data. For example, the residual block is set in such a way that the input x value is added to the output of the residual block, which induces the learning of a difference F(x) between input x and output H(x), not the output H(x) of the input data x. Accordingly, the previously learned input data x is taken as it stands and added to the output, so that only residual information F(x) is learned, thereby simplifying the model training process.

The generator is trained through differences between the output simulation images of the discriminator. That is, the simulation image $S_{AI}$ generated by the generator is compared with the simulation image $S_N$ generated based on the numerical model, and the comparison results are returned to the generator to improve the performance of the generator so as to output subsequent results that are more similar to the numerical model-based simulation image.

As described above, in the GAN model, the generator may synthesize an image through nonlinear mapping, and the discriminator may classify the generated image and a target image to be compared and generate a more precise image (i.e., a synthetic image close to the target image to be compared) with the increasing adversarial training iterations.

Referring back to FIG. 1, the step of generating an artificial intelligence model-based acoustic simulation image for an arbitrary position of the ultrasonic transducer using the trained artificial intelligence model (S500) is performed. Here, the arbitrary position refers to all transducer positions at which numerical model-based simulation has not been performed. That is, as a result of training the artificial intelligence model based on the simulation results for some preset positions, it is possible to output corresponding simulation images in real-time for all unlearned positions.

Figure 7:
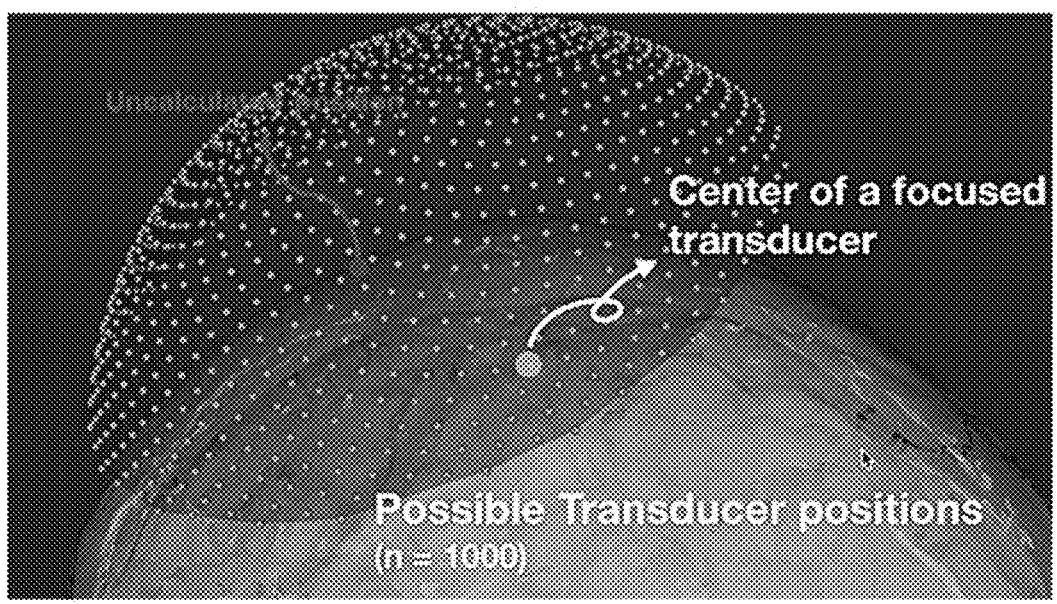
FIG. 7 shows a possible position range of an ultrasonic transducer and positions at which simulation is performed using a numerical model.

FIG. 7 shows the possible position range of the ultrasonic transducer and the positions at which simulation is performed using the numerical model. The blue area indicates the full range of motion of the transducer for ultrasound treatment, and the white points indicate a position (a center position of the transducer) at which ultrasound simulation is performed using the numerical model. The position indicated by the red arrow is a position at which numerical model-based simulation has not been performed, and with the trained artificial intelligence model, it is possible to know acoustic simulation results for the uncalculated position.

Figure 8:
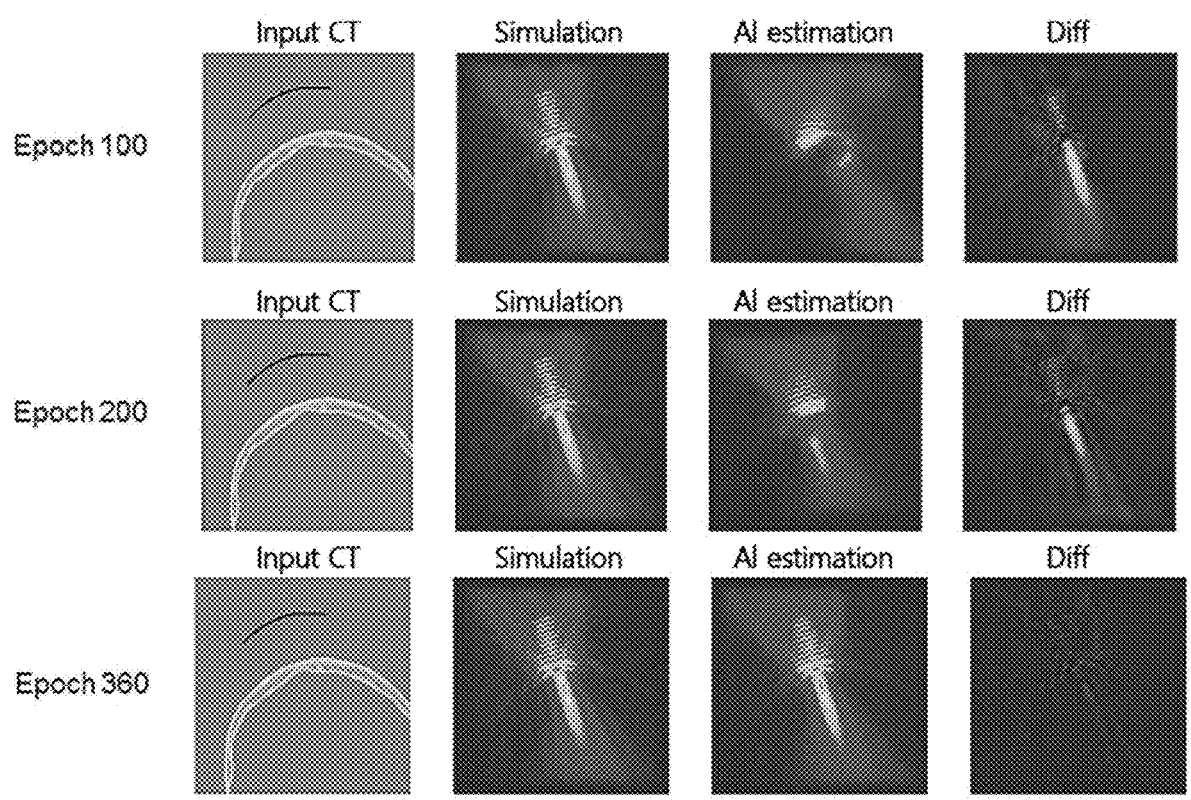
FIG. 8 shows that acoustic simulation results of an artificial intelligence model get closer to simulation results based on a numerical model with increasing training iterations.

FIG. 8 shows that the acoustic simulation results of the artificial intelligence model get closer to the simulation results based on the numerical model with the increasing training iterations. The simulation results when training is performed for 100, 200, and 360 iterations are shown in that order from the top. As shown, when training is performed at a small number of iterations (Epoch 100), there is a large difference between simulation (Simulation) results based on actual calculation and simulation (AI estimation) results generated by the artificial intelligence model, but as the number of iterations increases (Epoch 360), the generated simulation image gets closer to the simulation image based on actual calculation. As such, it can be seen that when training is iteratively performed over a predetermined number of iterations or more, there is almost no difference (Diff) between the two images.

Figure 9A:
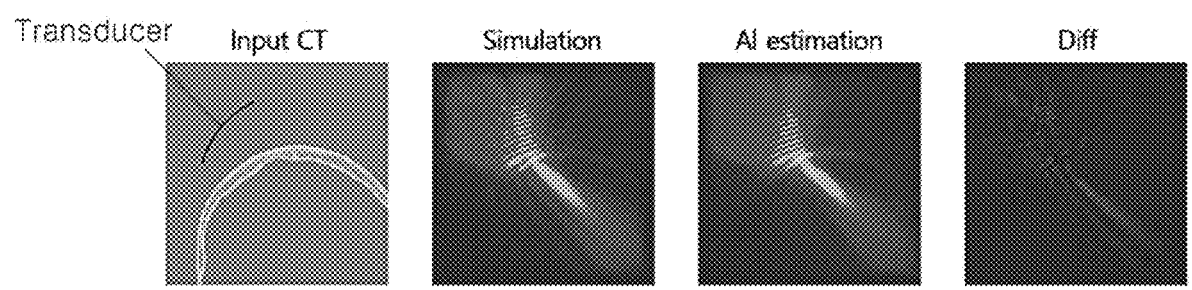
FIGS. 9A and 9B show acoustic simulation results with a position change of an ultrasonic transducer and differences between them.
Figure 9B:
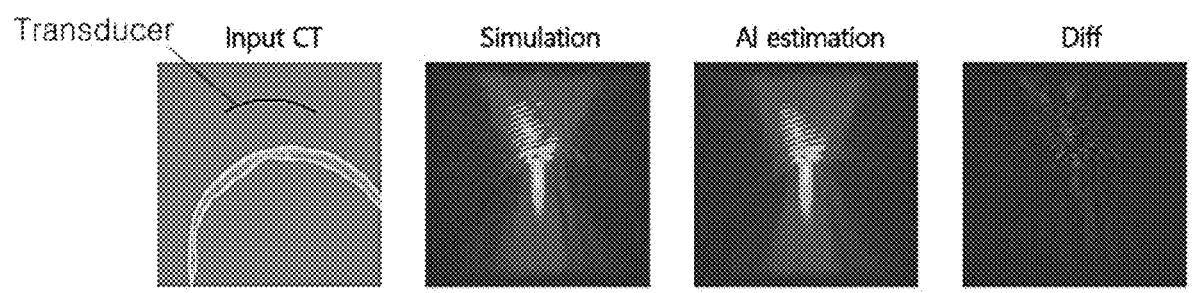

FIGS. 9A and 9B show the acoustic simulation results with a position change of the ultrasonic transducer and differences between them. The two results have gone through the sufficiently trained artificial intelligence model. As shown in FIGS. 9A and 9B, it can be seen that even when the position of the transducer is changed, there is almost no difference between the numerical model-based simulation results (Simulation) and the artificial intelligence model-based simulation results (AI estimation).

Figure 10A:
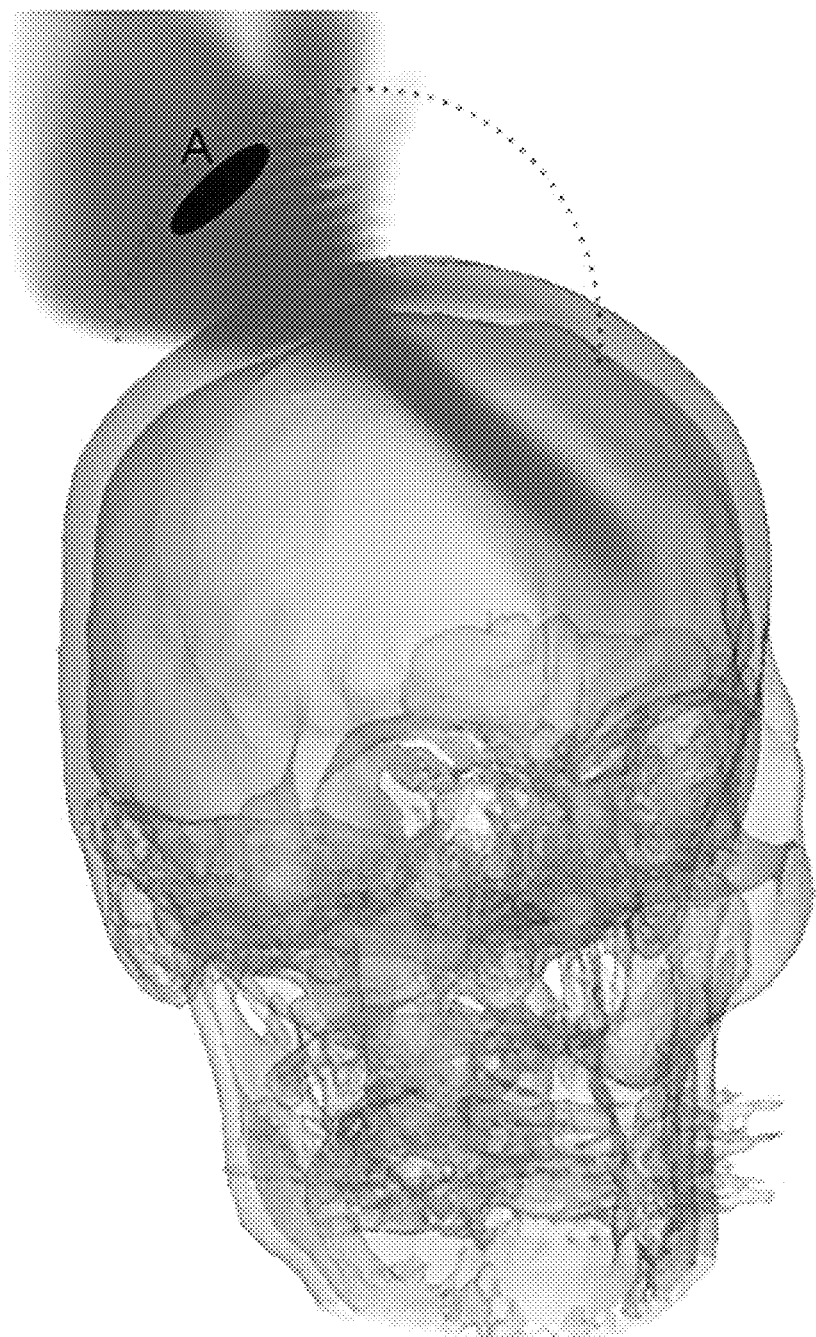
FIGS. 10A and 10B show 3D images of acoustic simulation results based on artificial intelligence with a position change of an ultrasonic transducer.
Figure 10B:
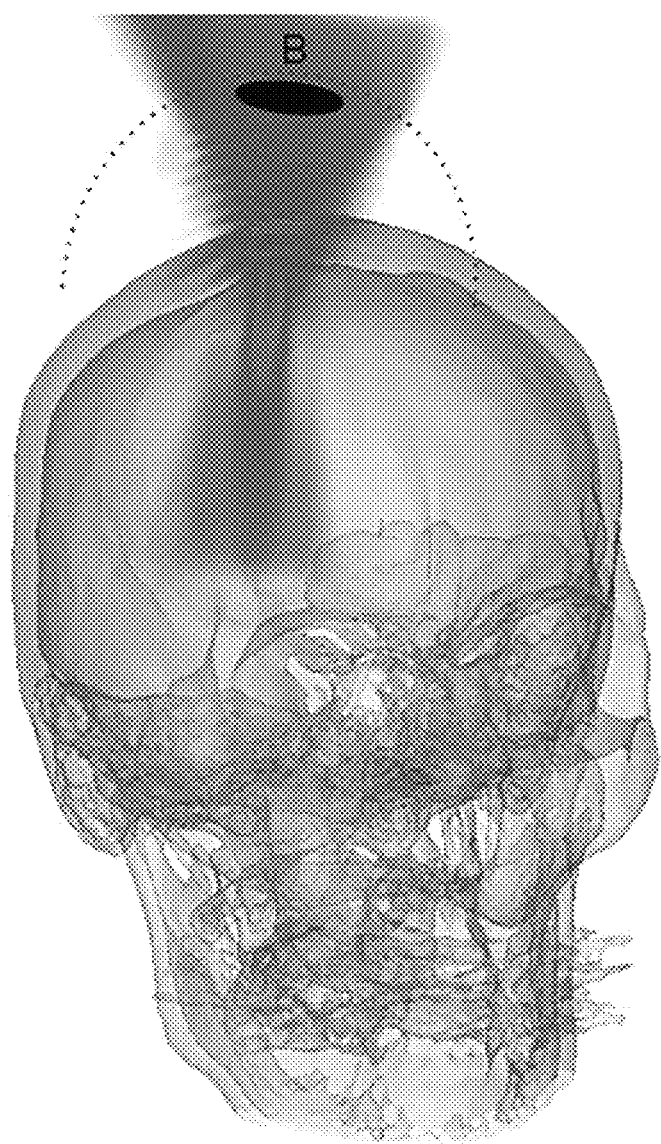

FIGS. 10A and 10B are 3D images of the acoustic simulation results based on artificial intelligence with a position change of the ultrasonic transducer. As the position of the transducer changes from A to B, the simulation results of the travel path and focal position of ultrasound and the acoustic pressure level at each position are differently measured. As a result of the experiment, the acoustic simulation results are outputted in real-time with a position change of the transducer.

The real-time acoustic simulation method based on artificial intelligence described above may be implemented as an application or in the format of program instructions that may be executed through a variety of computer components and recorded in computer-readable recording media. The computer-readable recording media may include program instructions, data files, and data structures alone or in combination.

Examples of the computer-readable recording media include hardware devices specially designed to store and execute the program instructions, for example, magnetic media such as hard disk, floppy disk and magnetic tape, optical media such as CD-ROM and DVD, magneto-optical media such as floptical disk, and ROM, RAM and flash memory.

Examples of the program instructions include machine code generated by a compiler as well as high-level language code that can be executed by a computer using an interpreter. The hardware device may be configured to act as one or more software modules to perform the processing according to the present disclosure, and vice versa.

According to the above-described embodiments, it is possible to acquire acoustic simulation results for an arbitrary transducer position at which simulation has never been performed before using the trained artificial intelligence model. The existing method that performs simulation through direct calculation needs to perform simulation for as many transducer positions as possible, and requires a few minutes or more for each position, which makes real-time simulation impossible. By contrast, according to the method of an embodiment, it is possible to perform real-time acoustic simulation for positions not included in the existing training data (i.e., positions at which calculation-based simulation has not been performed) at a very high speed using the artificial intelligence model.

Ultrasound Treatment System Based on Artificial Intelligence

Figure 11:
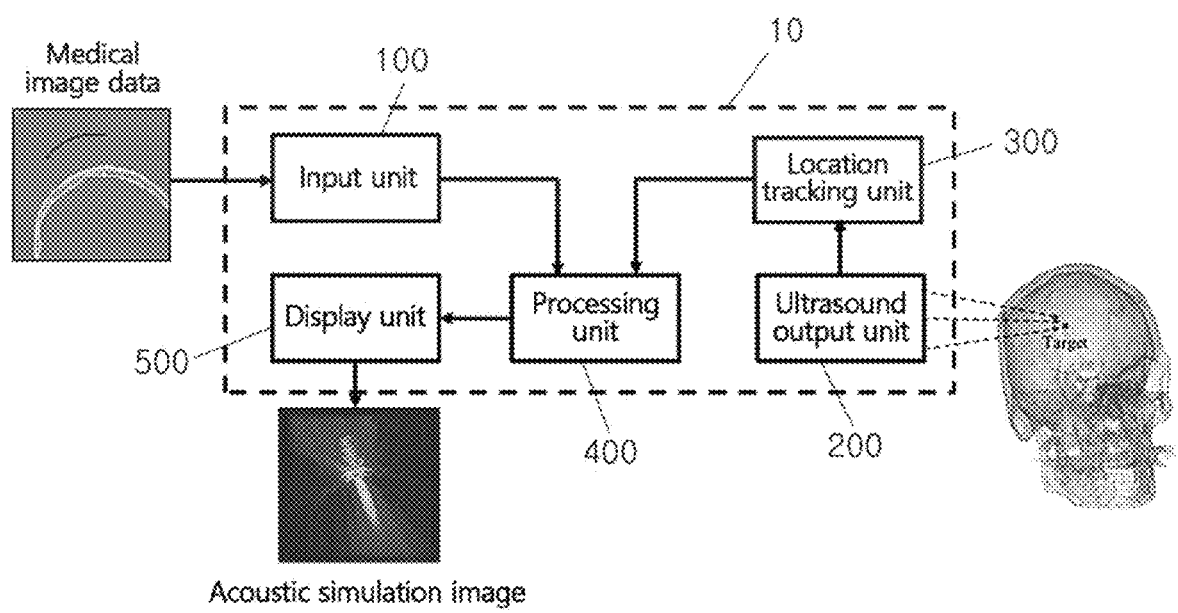
FIG. 11 shows a structure of an ultrasound treatment system based on artificial intelligence according to an embodiment.

FIG. 11 shows the structure of an ultrasound treatment system based on artificial intelligence according to an embodiment.

Referring to FIG. 11, the ultrasound treatment system 10 based on artificial intelligence according to an embodiment includes an input unit 100 to receive input medical image data of a target area to be treated, an ultrasound output unit 200 to output ultrasound to the target area, a location tracking unit 300 to acquire position information of the ultrasound output unit 200 in real-time, a processing unit 400 to generate a real-time acoustic simulation image with a position change of the ultrasound output unit 200 using an artificial intelligence model, and a display unit 500 to display the real-time acoustic simulation image.

The input unit 100 may receive an input CT or MRI image, and carry out additional preprocessing of the input image. The preprocessing process may include dividing the image into a region of interest and background through a mask and removing the background.

The ultrasound output unit 200 is a component that outputs ultrasound based on preset ultrasound parameters, includes a single ultrasonic transducer or a series of ultrasonic transducers to convert alternating current energy to mechanical vibration, and generates and outputs ultrasound according to the set value such as acoustic pressure, waveform, and frequency. The output ultrasound overlaps to form an ultrasound beam which in turn converges at a target focus point to remove or stimulate the target tissue. According to an embodiment, the ultrasound output unit 200 is configured to output high-intensity focused ultrasound to thermally or mechanically remove the target tissue or low-intensity focused ultrasound to stimulate the target tissue without damage.

The location tracking unit 300 detects a position change of the ultrasound output unit 200 using a component embedded or mounted in the ultrasound output unit 200 such as an accelerometer and a gyroscope, and transmits real-time position information to the processing unit 400.

The processing unit 400 includes at least one processor for performing the real-time acoustic simulation method based on artificial intelligence according to one of the above-described embodiments, and generates an acoustic simulation image corresponding to the transducer position using the position information of the ultrasound output unit 200 received from the location tracking unit 300.

The display unit 500 displays the generated acoustic simulation image on the display to allow the surgeon to perform ultrasound treatment while observing the target tissue.

According to the configuration of the ultrasound treatment system as described above, it is possible to acquire real-time acoustic simulation results for positions not included in the existing training data (i.e., positions at which calculation-based simulation has not been performed) using the artificial intelligence model. Through this, the medical staff can see simulation images with the movement of the ultrasonic transducer in real-time, thereby achieving faster and more precise treatment.

While the present disclosure has been hereinabove described with reference to the embodiments, it will be apparent to those having ordinary skill in the corresponding technical field that various modifications and changes may be made to the present disclosure without departing from the spirit and scope of the present disclosure defined in the appended claims.

What is claimed is:

1. A real-time acoustic simulation method based on artificial intelligence, performed by a processor, the method comprising:
    acquiring medical image data of a target area to be treated;
    determining ultrasound parameters related to the output of an ultrasonic transducer based on the medical image data;
    inputting the ultrasound parameters to a numerical model to generate a numerical model based acoustic simulation image for a specific position of the ultrasonic transducer;
    training an artificial intelligence model using the medical image data and the numerical model based acoustic simulation image;
    generating an artificial intelligence model based acoustic simulation image for an arbitrary position of the ultrasonic transducer using the trained artificial intelligence model; and
    outputting a real-time acoustic simulation image with a position change of the ultrasonic transducer.

2. The real-time acoustic simulation method based on artificial intelligence according to claim 1, wherein training the artificial intelligence model comprises:
    inputting the medical image data and the numerical model based acoustic simulation image as training data;
    generating an acoustic simulation image corresponding to a specific position of the ultrasonic transducer using a generator;
    acquiring error data by comparing the acoustic simulation image generated by the generator with the numerical model based acoustic simulation image using a discriminator; and
    training the generator using the error data.

3. The real-time acoustic simulation method based on artificial intelligence according to claim 2, wherein the artificial intelligence model is trained to reduce differences between the acoustic simulation image generated by the generator and the numerical model-based acoustic simulation image by iteratively performing the training step.

4. The real-time acoustic simulation method based on artificial intelligence according to claim 2, wherein the generator includes:
    at least one convolutional layer for receiving the input medical image data and outputting a feature map that emphasizes features of a region of interest; and
    at least one transposed convolutional layer for generating the acoustic simulation image corresponding to the medical image data based on the feature map.

5. The real-time acoustic simulation method based on artificial intelligence according to claim 2, wherein the discriminator includes at least one convolutional layer for receiving the input acoustic simulation image generated by the generator and outputting a feature map that emphasizes features of a region of interest.

6. The real-time acoustic simulation method based on artificial intelligence according to claim 1, wherein the artificial intelligence model generates the acoustic simulation image corresponding to the medical image data through trained nonlinear mapping.

7. The real-time acoustic simulation method based on artificial intelligence according to claim 1, wherein the medical image data includes a computed tomography (CT) image or a magnetic resonance imaging (MRI) image.

8. A computer program stored in a non-transitory computer-readable recording medium for performing the real-time acoustic simulation method based on artificial intelligence according to claim 1.

9. An ultrasound treatment system based on artificial intelligence, comprising:
    an input unit to receive input medical image data of a target area to be treated;
    an ultrasound output unit to output ultrasound to the target area;
    a location tracking unit to acquire position information of the ultrasound output unit in real-time;
    a processing unit to generate a real-time acoustic simulation image with a position change of the ultrasound output unit using the method according to claim 1; and
    a display unit to display the real-time acoustic simulation image.

10. The ultrasound treatment system based on artificial intelligence according to claim 9, wherein the ultrasound output unit is configured to output high-intensity focused ultrasound to thermally or mechanically remove a target tissue or low-intensity focused ultrasound to stimulate the target tissue without damage.

11. A real-time acoustic simulation method based on artificial intelligence, performed by a processor, the method comprising:
    acquiring medical image data of a target area to be treated and reference position information of an ultrasonic transducer;
    inputting the ultrasound parameters to a numerical model to generate a numerical model based acoustic simulation image for a specific position of the ultrasonic transducer;
    generating an acoustic simulation image for an arbitrary position of the ultrasonic transducer using an artificial intelligence model trained to generate the acoustic simulation image in response to a position change of the ultrasonic transducer, wherein the artificial intelligence model is trained to reduce differences between the acoustic simulation image generated by the generator and the numerical model based acoustic simulation image; and outputting the acoustic simulation image according to a position change of the ultrasonic transducer.

12. The real-time acoustic simulation method based on artificial intelligence according to claim 11, wherein the training of the artificial intelligence model comprises:

receiving input of the medical image data and the numerical model based acoustic simulation image as training data;

generating an acoustic simulation image corresponding to a specific position of the ultrasonic transducer using a generator;

acquiring error data by comparing the acoustic simulation image generated by the generator with the numerical model based acoustic simulation image using a discriminator; and training the generator using the error data.

13. An ultrasound treatment system based on artificial intelligence, comprising:

an input unit to receive input medical image data of a target area to be treated;

an ultrasound output unit to output ultrasound to the target area;

a location tracking unit to acquire position information of the ultrasound output unit in real time;

a processing unit to generate a real-time acoustic simulation image with a position change of the ultrasound output unit using the method according to claim 11; and a display unit to display the real-time acoustic simulation image.

* * * * *